United States Patent [19]
Britton et al.

[11] Patent Number: 5,420,266
[45] Date of Patent: May 30, 1995

[54] PROCESS FOR ANOMERIZING NUCLEOSIDES

[75] Inventors: Thomas C. Britton, Carmel; Michael E. LeTourneau, Indianapolis, both of Ind.

[73] Assignee: Eli Lilly and Company, Indianapolis, Ind.

[21] Appl. No.: 176,981

[22] Filed: Jan. 3, 1994

Related U.S. Application Data

[63] Continuation of Ser. No. 938,791, Sep. 1, 1992, abandoned.

[51] Int. Cl.$^6$ ............................................. C07H 19/06
[52] U.S. Cl. .............................. 536/28.52; 536/28.1; 536/28.2; 536/28.5; 536/28.51
[58] Field of Search ................. 536/28.52, 28.53, 28.1, 536/28.2, 28.51

[56] References Cited

PUBLICATIONS

Armstrong et al., Nucleic Acid Research, vol. 3, No. 7, pp. 1791-1810, (1976).
Inoue et al., Heterocycles, vol. 8, pp. 427-432 (1977).

*Primary Examiner*—Douglas W. Robinson
*Assistant Examiner*—James Oliver Wilson
*Attorney, Agent, or Firm*—Robert A. Conrad

[57] ABSTRACT

A process for increasing the amount of a desired anomer nucleoside from an undesired anomeric nucleoside mixture thereof by contacting the mixture with a hydroxide base in an organic solvent.

43 Claims, No Drawings

PROCESS FOR ANOMERIZING NUCLEOSIDES

This application is a continuation of application Ser. No. 07/938,791, filed on Sep. 1, 1992, now abandoned.

BACKGROUND OF THE INVENTION

1. Field of the Invention

The invention relates to the field of pharmaceutical and organic chemistry and pertains to a process for anomerizing nucleosides.

2. State of the Art

Processes for preparing nucleosides frequently result in a mixture of alpha and beta nucleoside anomers. These nucleoside anomers are typically separated by a physical means such as crystallization or chromatography. Most often, the desired biological activity of a nucleoside resides predominantly in a single anomer of an anomeric mixture. However, the amount of a specified nucleoside anomer recoverable from an anomeric mixture by the above mentioned separation methods is often substantially less than that originally present in the anomeric mixture. Such low recoveries are generally due to interference from increased proportions of the unwanted anomer as the separation proceeds. Beta nucleoside anomers are useful and important as pharmacologically active compounds. Anomerization provides a way of increasing the amount of a desired nucleoside anomer over that originally present in an anomeric mixture. When used in conjunction with the aforementioned separation methods, anomerization can afford substantially improved overall recoveries of a desired nucleoside anomer.

Nucleoside anomerization has been accomplished by photoirradiation in water, see R. A. Sanchez, et al., *J. Mol. Biol.*, 47, 531–543 (1970); and with bromine, see H. Quelo, et. al., *C. R. Acad. Sci., Ser. C*, 275, 1137–1140 (1972).

J. Cadet, et al., describe nucleoside anomerization in "Nucleic Acid Hydrolysis I. Isomerization and Anomerization of Pyrimidic Deoxyribonucleosides in an Acidic Medium.", *J. Amer. Chem. Soc.*, 96:20, 6517–6519 (1974) which involves contacting thymidine and 2'-deoxyuridine nucleosides with 2M $HClO_4$ at 90° C. to make α- and β-furanosidic and pyranosidic anomers.

Yamaguchi, T., et. al., in "Synthetic Nucleosides and Nucleotides. XXI. On the Synthesis and Biological Evaluations of 2'-Deoxy-alpha-D-ribofuranosyl Nucleosides and Nucleotides", *Chem. Pharm. Bull.*, 32(4), 1441–1450 (1984) describe anomerizing β-3',5'-di-O-p-toluoyl-2'-deoxythymidine and β-$N^4$-benzoyl-2'-deoxycytidine with bis(trimethylsilyl)acetamide and trimethylsilyltrifluoromethanesulfonate in dry acetonitrile at 70° C.

Nucleoside anomerization employing protic acids or Lewis acids have been applied to a wide variety of nucleosides and include for example: 2M HCl, see F. Seela and H. D. Winkler, *Carbohydrate Research*, 118, 29–53 (1983); 1M HBr, see J. Cadet, *Tetrahedron Lett.*, 867–870 (1974); and NaI/HOAc, see J. Matulic-Adamic, et. al., *J. Chem. Soc.*, 2681–2686 (1988).

Base catalyzed anomerization has also been reported. For example, Armstrong, V. W., et al., in "The Base Catalyzed Anomerization of β-5-Formyluridine; Crystal and Molecular Structure of α-5-Formyluridine", *Nucleic Acid Res.*, 3, 1791 (1976) describe the treatment of β-5-formyluridine with 1:1 4N aqueous NaOH:- MeOH at room temperature which affords an anomerically mixed product. However, uridine and 5-bromouridine are not anomerized by this process since they lack the 5-formyl group on the nucleoside substrate. I., Hideo, et al., "Synthesis of 5-Alkyl and 5-Acyl-uridines via 6-Mercaptouridine (Nucleosides and Nucleotides XVII)", *Heterocycles*, 8, 427–432 (1977) describe the anomerization of 2',3'-O-isopropylidene-5-acetyl-α-uridine with 2N sodium hydroxide. As can be seen, base catalyzed anomerization has been limited to pyrimidine nucleosides having electron-withdrawing substituents (e.g. formyl or acetyl groups) at the C-5 position of the heterocyclic portion of the nucleoside.

An object of the present invention is to provide a base catalyzed process for anomerizing nucleosides.

Another object of this invention is to provide a base catalyzed process for anomerizing 2'-deoxy-2',2'-difluoro-nucleosides.

Another object of this invention is to provide a base catalyzed process for anomerizing alpha-anomer-enriched nucleosides free of the disadvantages and limitations found in the prior art.

Another object of this invention is to provide a base catalyzed process for anomerizing beta-anomer-enriched nucleosides free of the disadvantages and limitations found in the prior art.

SUMMARY OF THE INVENTION

The invention is a process for increasing the amount of beta nucleoside anomer of the formula

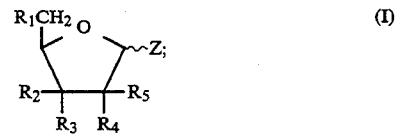

(I)

wherein $R_1$ is selected from the group consisting of hydrogen, lower alkyl, fluoro, azide, hydroxy, and OB where B is a lower alkyl, or base-stable hydroxy protecting group; $R_2$ is selected from the group consisting of hydrogen, azide, lower alkyl, fluoro, hydroxy (provided $R_3$ cannot be fluoro, azide, or hydroxy), and OB where B is as defined above; $R_3$ is selected from the group consisting of hydrogen, azide, lower alkyl, fluoro, hydroxy (provided $R_2$ cannot be fluoro, azide or hydroxy), and OB where B is as defined above; $R_4$ is selected from the group consisting of hydrogen, azide, lower alkyl, fluoro, hydroxy (provided $R_5$ cannot be fluoro, azide or hydroxy), and OB where B is as defined above; $R_5$ is selected from the group consisting of hydrogen, azide, lower alkyl, fluoro, hydroxy (provided $R_4$ cannot be fluoro, azide or hydroxy), and OB where B is as defined above; and Z is a nucleobase of the formula

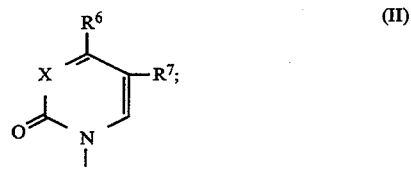

(II)

wherein X is selected from N and $CR_8$ where $R_8$ is hydrogen or lower alkyl; $R_6$ is selected from the group consisting of amino, lower alkyl amino, di(lower alkyl)

amino, acyl amino, and N-acyl lower alkyl amino; and $R_7$ is selected from the group consisting of hydrogen, lower alkyl, fluoro and lower alkenyl;
in an alpha-anomer-enriched nucleoside over that originally present; comprising contacting an alpha-anomer-enriched nucleoside of formula I with a hydroxide base in an organic solvent.

In another aspect the invention is a process for increasing the amount of alpha nucleoside anomer of formula I in a beta-anomer-enriched nucleoside over that originally present; comprising contacting a beta-anomer-enriched nucleoside of formula I with a hydroxide base in an organic solvent.

DETAILED DESCRIPTION OF THE INVENTION

Throughout this document, all temperatures are in degrees Celsius and all proportions, percentages and the like, are in weight units. Mixtures of solvents are in volume units, except where otherwise indicated. Anomeric mixtures are expressed as a weight/weight ratio. The structural drawings shown herein are not indicative of the stereochemistry of the compounds since compounds of all configurations are believed to be useful and the stereochemistry of them is accordingly not a limitation. The phrase "anomer enriched" alone or in combination refers to an anomeric mixture wherein the anomeric ratio differs from the equilibrium anomeric ratio and includes substantially pure anomers. The term "lower alkyl" alone or in combination refers to straight, cyclic and branched chain aliphatic hydrocarbon groups which preferably contain up to 7 carbon atoms such as methyl, ethyl, n-propyl, isopropyl, n-butyl, t-butyl, n-pentyl, n-hexyl, 3-methylpentyl groups and the like. The term "aryl" alone or in combination refers to carbocyclic or heterocyclic groups such as phenyl, naphthyl, thienyl and substituted derivatives thereof. The term "acyl" alone or in combination refers to the general formula ACO; wherein A is lower alkyl or aryl. The term "lower alkenyl" refers to an unsaturated hydrocarbon group containing up to 7 carbon atoms and having one or two carbon double bonds. The phrase "base-stable hydroxy protecting group" refers to hydroxy protecting groups stable under basic conditions as described in Chapter 3 of *Protective Groups in Organic Chemistry*, McOmie Ed., Plenum Press, New York (1973) and Chapter 2 of *Protective Groups in Organic Synthesis*, Green, John, J. Wiley and Sons, New York (1981) such as benzyloxymethyl, methoxymethyl, 2-tetrahydropyranyl, benzyl, p-methoxybenzyl and trityl; and where the nucleoside contains a cis-2',3'-diol derivative the base-stable hydroxy protecting group includes acetonide, benzylidene and p-methoxybenzylidene.

The present process is carried out by contacting an alpha- or beta-anomer-enriched nucleoside of formula I with a hydroxide base in an organic solvent. The process promotes the stereoconversion of nucleosides by inverting the absolute configuration at the C-1' position of the nucleoside. While not wishing to be bound by theory, it is believed that this inversion is achieved by the action of the hydroxide base, hydroxide base concentration, solvent, and reaction temperature employed.

The present process increases the amount of a desired nucleoside anomer present in an anomeric mixture of unprotected nucleosides and nucleosides that are typically unreactive to acid catalyzed anomerization processes.

In the case where it is desirable to increase the proportion of beta anomer, a preferred embodiment of the present process, employs an alpha-anomer-enriched nucleoside having an anomeric ratio ranging from at least 10:90 alpha to beta up to substantially pure (about 100:0 alpha anomer; and more preferably ranging from about 50:50 alpha to beta up to substantially pure alpha anomer.

In the case where it is desirable to increase the proportion of alpha anomer, a preferred embodiment of the present process, employs a beta-anomer-enriched nucleoside having an anomeric ratio ranging from at least 10:90 beta to alpha up to substantially pure beta anomer; more preferably ranging from about 50:50 beta to alpha up to substantially pure beta anomer.

A particularly preferred embodiment of the present process, increases the amount of 2',2'-difluoro-2'-deoxy-β-anomer nucleoside in anomeric mixture and employs alpha-anomer-enriched 2',2'-difluoro-2'-deoxynucleosides having an anomeric ratio ranging from at least 75:25 alpha to beta up to substantially pure alpha anomer.

Hydroxide bases useful in the present process include alkali metal hydroxides such as lithium hydroxide, sodium hydroxide, potassium hydroxide and cesium hydroxide monohydrate; quaternary ammonium hydroxide bases such as benzyltrimethylammonium hydroxide and tetramethylammonium hydroxide; and alkaline earth metal hydroxides; most preferred are alkali metal hydroxides such as potassium hydroxide and cesium hydroxide monohydrate. The amount of hydroxide base employed in the present process ranges from about 2 molar equivalents to about 40 molar equivalents; however, from about 2.5 molar equivalents to about 5 molar equivalents is preferred.

It has been found that the rate of anomerization exhibits a third order dependence on the hydroxide base concentration. Therefore, the concentration of hydroxide base employed preferably ranges from about 0.5 molar to about 5 molar and more preferably ranges from about 2 molar to about 4 molar.

Solvents useful in the present process are lower alcohols such as methanol, ethanol, 2-methoxyethanol, and mixtures thereof; preferred is methanol.

The reaction time is a function of the reactivity of the nucleoside, the hydroxide base, the hydroxide base concentration and the reaction temperature employed. The present process is preferably carried out at temperatures ranging from room temperatures to about 120° C.; more preferably from about 40° C. to about 120° C.; and most preferably from about 40° C. to about 80° C. The present process is carried out in about ½ hour to 5 days.

The present process shifts the anomeric ratio of an anomer enriched nucleoside towards its equilibrium anomeric ratio. The equilibrium anomeric ratio differs for each nucleoside. For anomeric mixtures of 1-(2'-deoxy-2',2'-difluororibofuranosyl)-4-aminopyrimidin-2-one this is approximately 60(β):40(α). It should be noted that the reaction rate decreases substantially as the equilibrium anomeric ratio is approached. Therefore, the present process is carried out, in either a batch, semi-batch or continuous mode, it may be desirable to stop the process prior to reaching the equilibrium anomeric ratio in order to avoid yield losses due to competing reactions, e.g. hydrolysis.

When the present process is carried out in the presence of water, the potential for producing hydrolysis products, e.g. the conversion of the cytosine moiety to uracil, increases. However, we have found that when the present process is carried out with substantially anhydrous organic solvents, the hydrolysis reaction is suppressed and substantially higher yield of the anomerization product results. Therefore, the amount of water employed in the present process is substantially zero.

The process may be monitored by withdrawing aliquots at various times over the course of the reaction, quenching the aliquots with acid, diluting the aliquots with an appropriate volume with water, and assaying the aliquots by high pressure liquid chromatography (HPLC) to determine the anomer ratio of the nucleosides present.

Once the desired anomer ratio has been achieved, the resulting solution is acidified, for example, by adding an acid such as hydrochloric acid, or neutralized, depending on the nucleoside employed.

The desired nucleoside anomer may be isolated by standard separation techniques such as crystallization or chromatography.

The following examples illustrate specific aspects of the present invention and are not intended to limit the scope thereof in any respect and should not be so construed.

EXAMPLE 1

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Anhydrous Lithium Hydroxide in Methanol A solution of 1.50 g (5.70 mmol) of 1 in 6.0 ml of anhydrous methanol was treated with 410 mg (17.1 mmol; 3.0 eq.) of anhydrous lithium hydroxide and the resulting mixture was heated to reflux under dry nitrogen. Reaction aliquots (0.100 ml, 1.40% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | 0.33 | 99.6 | 0.4 | 100:0 |
| 2 | 24.50 | 64 | 18 | 79:21 |
| 3 | 51.25 | 42 | 24 | 64:36 |
| 4 | 71.50 | 34 | 24 | 58:42 |
| 5 | 94.75 | 27 | 24 | 53:47 |

Method A: Column: 25 cm×4.6 mm Zorbax RX reverse phase. Flow rate: 1.2 ml/min. Solvent A: methanol. Solvent B: 0.1M pH 3 phosphate buffer. Gradient program: 0–8.0 minutes isocratic 3/97 of A/B; 8.0–13.0 minutes linear gradient from 3/97 of A/B to 50/50 of A/B: 13.0–18.0 minutes isocratic 50/50 of A/B; 18.0–23.0 minutes linear gradient from 50/50 of A/B to 3/97 of A/B. The peak areas of 1 ($t_r$=4.9 minutes) and 2 ($t_r$=7.2 minutes) were compared to an external standard containing known quantities of authentic samples to provide the yields of each.

EXAMPLE 2

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Anhydrous Sodium Hydroxide in Methanol A solution of anhydrous sodium hydroxide in methanol was prepared by adding 6.0 ml of anhydrous methanol, stirred at 25° C. under dry nitrogen, to 393 mg (17.1 mmol, 3.0 eq.) of sodium metal. When the metal dissolved, water (306 μl, 17.0 mmol, 3.0 eq.) was added. To the above solution was added 1.50 g (5.70 mmol) of 1, and the resulting mixture was heated to reflux. Reaction aliquots (0.100 ml, 1.36% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .33 | 99 | 0.7 | >99:1 |
| 2 | 1.50 | 92 | 6 | 94:6 |
| 3 | 18.50 | 40 | 30 | 57:43 |
| 4 | 23.00 | 34 | 30 | 53:47 |
| 5 | 25.75 | 31 | 30 | 51:49 |
| 6 | 90.75 | 13 | 18 | 43:57 |

EXAMPLE 3

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Potassium Hydroxide in Ethanol A solution of 1.50 g (5.70 mmol) of 1 in 6.0 ml of absolute ethanol was treated with 1.10 g (17.1 mmol; 3.0 eq.) of 86 percent potassium hydroxide and the resulting mixture was heated to 76° C.–77° C. under dry nitrogen. Reaction aliquots (0.100 ml, 1.26% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .33 | 93 | 5 | 95:5 |
| 2 | 2.00 | 49 | 22 | 69:31 |
| 3 | 4.50 | 24 | 23 | 51:49 |
| 4 | 6.50 | 17 | 21 | 45:55 |
| 5 | 24.33 | 4 | 6 | 39:61 |
| 6 | 29.00 | 3 | 5 | 39:61 |

EXAMPLE 4

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Barium Hydroxide in Methanol A mixture of 0.60 g (2.28 mmol; 1.0 eq.) of 1, 0.62 g (3.42 mmol; 1.5 eq.) of 95 percent barium hydroxide and 4.4 ml of anhydrous methanol was stirred and heated at reflux for 28 hours. The resulting mixture was cooled to 0° C., quenched with 5.6 ml of 1N HCl, and diluted to 250 ml with water. A 5.00 ml aliquot of the resulting tan solution was diluted to 100.0 ml with water, and assayed by HPLC (Method A). The yield of 1 and 2 and their anomeric ratio (1:2) is tabulated below:

| % Yield 1 | % Yield 2 | Ratio 1:2 |
| --- | --- | --- |
| 82 | 8 | 92:8 |

EXAMPLE 5

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Cesium Hydroxide Monohydrate in Methanol A mixture of 1.23 g (4.68 mmol) of 1, 2.36 g (14.05 mmol; 3.0 eq.) of cesium hydroxide monohydrate, and 4.93 ml of anhydrous methanol was heated to reflux under dry nitrogen. Reaction aliquots (0.100 ml, 1.59% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .33 | 97 | 3 | 97:3 |
| 2 | 2.50 | 73 | 21 | 78:22 |
| 3 | 4.50 | 58 | 31 | 65:35 |
| 4 | 7.00 | 48 | 37 | 56:44 |
| 5 | 24.00 | 23 | 32 | 41:59 |

EXAMPLE 6

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Potassium Hydroxide in 2-Methoxyethanol A mixture of 1.50 g (5.70 retool) of 1, 1.10 g (16.9 mmol; 3.0 eq.) of 86 percent potassium hydroxide, and 6.0 ml of 2-methoxyethanol was heated to 76° C. under dry nitrogen. Reaction aliquots (0.100 ml, 1.26% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .42 | 93 | 4 | 96:4 |
| 2 | 2.08 | 62 | 17 | 78:22 |
| 3 | 4.58 | 38 | 23 | 62:38 |
| 4 | 6.58 | 29 | 24 | 54:46 |
| 5 | 24.50 | 6 | 12 | 36:64 |
| 6 | 29.08 | 5 | 10 | 35:65 |

EXAMPLE 7

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Potassium Hydroxide in Methanol A mixture of 750 mg (2.85 mmol) of 1, 558 mg (8.55 mmol; 3.0 eq.) of 86 percent potassium hydroxide, and 3.4 ml of anhydrous methanol was heated to reflux under dry nitrogen. Reaction aliquots (0.100 ml, 2.58% of the total) were withdrawn at the times indicated below, quenched with 5 ml 1N HCl, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .33 | 99 | 1 | 99:1 |
| 2 | 2.17 | 88 | 12 | 88:12 |
| 3 | 3.50 | 78 | 18 | 81:19 |
| 4 | 4.92 | 70 | 22 | 76:24 |
| 5 | 24.00 | 29 | 34 | 46:54 |
| 6 | 29.00 | 27 | 34 | 44:56 |
| 7 | 47.25 | 21 | 29 | 42:58 |

EXAMPLE 8

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Potassium Hydroxide in Methanol A mixture of 1.50 g (5.70 mmol) of 1, 1.10 g (16.9 mmol; 3.0 eq.) of 86 percent potassium hydroxide and 4.4 ml of anhydrous methanol was heated to 55° C. under dry nitrogen. Reaction aliquots (0.100 ml, 1.72% of the total) were withdrawn at the times indicated below, quenched with 5 ml 1N HCl, diluted to 100. 0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
| --- | --- | --- | --- | --- |
| 1 | .33 | 99 | 1 | 99:1 |
| 2 | 4.17 | 87 | 11 | 89:11 |
| 3 | 24.50 | 52 | 35 | 60:40 |
| 4 | 27.58 | 49 | 35 | 58:42 |
| 5 | 45.25 | 37 | 38 | 50:50 |

EXAMPLE 9

Anomerization of
1-(2'-deoxy-2',2'-difluoro-α-D-ribofuranosyl)-4-aminopyrimidin-2-one (1) to
1-(2'-deoxy-2',2'-difluoro-β-D-ribofuranosyl)-4-aminopyrimidin-2-one (2) with Benzyltrimethylammonium Hydroxide in Methanol Three identical mixtures of 250 mg (0.95 mmol) of 1 and 1.3 ml (2.85 mmol, 3.0 eq.) of N-benzyltrimethylammonium hydroxide (40% by weight in methanol) were heated at reflux under dry nitrogen for the times indicated below. The resulting solutions (1–3) were cooled to 25° C. and each was quenched by the adding 10 ml of 1.0N HCl, diluted to 1L with water, and assayed by HPLC (Method A). The yields of 1 and 2 and their anomeric ratios (1:2) are tabulated below:

| Solution | Reflux Time (Hrs.) | % Yield 1 | % Yield 2 | Ratio 1:2 |
|---|---|---|---|---|
| 1 | 3.0 | 65 | 15 | 81:19 |
| 2 | 5.5 | 52 | 22 | 71:29 |
| 3 | 8.0 | 35 | 24 | 59:41 |

COMPARATIVE EXAMPLE 10

Anomerization of
1-(2'-deoxy-2',2'-difluoro-α-D-ribofuranosyl)-4-aminopyrimidin-2-one Hydrochloride (1·HCl) to
1-(2'-deoxy-2',2'-difluoro-β-D-ribofuranosyl)-4-aminopyrimidin-2-one (2) with Aqueous Sodium Hydroxide This example illustrates the effect water has on the nucleoside anomer yield. A solution of 160 mg (0.53 mmol; 1.0 eq.) of 1·HCl in 40 ml of 2.0N aqueous NaOH (80 mmol, 150 eq.) was heated at 60° C. Reaction aliquots (4.00 ml, 10.0% of the total) were withdrawn at the indicated times, quenched with 10 ml of 1N HCl, diluted to 50.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
|---|---|---|---|---|
| 1 | 1.0 | 68 | 10 | 87:13 |
| 2 | 3.0 | 35 | 13 | 73:27 |
| 3 | 6.0 | 12 | 8 | 62:38 |
| 4 | 24.0 | 0 | 0 | — |

EXAMPLE 11

Anomerization of a crude 81:19 mixture of
1-(2'-deoxy-2',2'-difluoro-α-D-ribofuranosyl)-4-aminopyrimidin-2-one (1) and
1-(2'-deoxy-2',2'-difluoro-β-D-ribo--furanosyl)-4-aminopyrimidin-2-one (2) with Potassium Hydroxide in Methanol The selective crystallization of 2 from a crude aqueous mixture of 1 and 2 having an anomeric ratio (1:2) of 65:35 provided a mother liquor having an anomeric ratio of 81:19. On evaporating the liquor in vacuo 36.14 g of residue was obtained which was found by HPLC analysis to contain 18.32 g (0.070 moles) of total nucleoside (1 and 2). A solution of the above residue, 13.7 g (0.210 moles; 3.0 eq.) of 86 percent potassium hydroxide and 120 ml of methanol was heated at reflux under dry nitrogen. After 8.25 hours, an additional 2.3 g (0.035 moles) of 86 percent potassium hydroxide was added over a 10 minute period. Reaction aliquots (0.100 ml, 0.0645% of the total) were withdrawn at the times indicated below, quenched with 5 ml 1N HC, diluted to 100.0 ml with water and assayed by HPLC (Method A). The yields of 1 and 2 and their anomeric ratios (1:2) are tabulated below:

| Aliquot | Elapsed Time (Hrs.) | % Yield 1 | % Yield 2 | Ratio 1:2 |
|---|---|---|---|---|
| 1 | .42 | 81 | 19 | 81:19 |
| 2 | 7.50 | 70 | 24 | 75:25 |
| 3 | 8.25 | 70 | 25 | 74:26 |
| 4 | 27.50 | 49 | 36 | 58:42 |

EXAMPLE 12

Anomerization of
1-(2'-deoxy-2',2'-difluoro-α-D-ribofuranosyl)-4-aminopyrimidin-2-one Hydrochloride (1·HCl) to
1-(2'-deoxy-2',2'-difluoro-β-D-ribofuranosyl)-4-aminopyrimidin-2-one (2) Potassium Hydroxide in Methanol A mixture of 1.60 g (5.34 mmol) of 1·HCl, 1.40 g (21.5 mmol; 4.0 eq.) of 86 percent potassium hydroxide, and 7.5 ml of anhydrous methanol was heated at reflux under dry nitrogen. Reaction aliquots (0.135 ml, 1.47% of the total) were withdrawn at the times indicated below, quenched with 5 ml of 1N HCl, diluted to 100.0 ml with water and assayed by HPLC (Method A). The yields of 1 and 2 and their anomeric ratios (1:2) are tabulated below:

| Aliquot | Elapsed Time (Hrs) | % Yield 1 | % Yield 2 | Ratio 1:2 |
|---|---|---|---|---|
| 1 | 1.08 | 95 | 4 | 96:4 |
| 2 | 4.33 | 82 | 14 | 85:15 |
| 3 | 7.08 | 73 | 21 | 77:23 |
| 4 | 23.08 | 45 | 38 | 55:45 |
| 5 | 29.58 | 39 | 40 | 50:50 |

After refluxing for 30 hours, the reaction mixture was cooled in an ice bath and acidified by the dropwise addition of 1.5 ml of concentrated HCl. The resulting mixture was filtered to remove the precipitated salts and the filter cake was washed with methanol (3×5 ml portions). The filtrate was then evaporated in vacuo and the residue dissolved in 7 ml of water. The pH of the aqueous solution was adjusted to 7 with aqueous potassium hydroxide and the solution was concentrated in vacuo until crystallization ensued. Upon cooling for 16 hours at 5° C.–10° C. 328 mg (after air drying) of off-white precipitate were obtained and shown by $^1$H NMR and HPLC analysis (Method A) to be 83.9 percent of 2 and contained 1 percent total non-volatile impurities, for a 21 percent isolated yield of 2.

EXAMPLE 13

Anomerization of
1-(β-D-ribofuranosyl)-4-aminopyrimidin-2-one (3) to
1-(α-D-ribofuranosyl)-4-aminopyrimidin-2-one (4) with Potassium Hydroxide in Methanol A mixture of 2.43 g (10.0 mmol) of 3, 1.68 g (30.0 mmol; 3.0 eq.) of 86 percent potassium hydroxide and 14.5 ml of anhydrous methanol was heated at reflux under dry nitrogen. Reaction aliquots (0.100 ml, 0.603% of the total) were withdrawn at the times indicated below, quenched with 5 ml 1N HCl, diluted to 100.0 ml with water and assayed by HPLC (Method B). The yields of 3 and 4 and their anomeric ratios (3:4) are tabulated below:

| Aliquot | Elapsed Time (Hrs.) | % Yield 3 | % Yield 4 | Ratio 3:4 |
|---|---|---|---|---|
| 1 | 0.5 | 100 | 0 | 100:0 |
| 2 | 24.1 | 87 | 4 | 96:4 |
| 3 | 49.6 | 78 | 5 | 94:6 |
| 4 | 95.8 | 67 | 5 | 93:7 |
| 5 | 169.3 | 55 | 4 | 93:7 |

Method B: Column: 0.25 cm×4.6 mm zorbax RX reverse phase Flow rate: 1.2 ml/minute. Solvent A: methanol. Solvent B: 0.1M pH 7 phosphate buffer. Gradient: 0–8.0 minutes isocratic 100% of B; 8.0–13.0 minutes linear gradient from 100% of B to 50/50 of A/B: 13.0–18.0 minutes isocratic 50/50 of A/B; 18.0–23.0 minutes linear gradient from 50/50 of A/B to 100% of B. The peak areas of 3 ($t_r$=6.4 minutes) and 4 ($t_r$=6.0 minutes) were compared to an external standard containing known quantities of authentic samples to provide the yields of each.

EXAMPLE 14

Anomerization of 1-(2'-deoxy-α-D-ribofuranosyl)-4-aminopyrimidin-2-one (5) to 1-(2'-deoxy-β-D-ribofuranosyl)-4-aminopyrimidin-2-one (6) with Potassium Hydroxide in Methanol A mixture of 1.14 g (5.0 mmol) of 5, 7.5 ml of methanol and 990 mg (15.0 mmoles; 3.0 eq.) of 85 percent potassium hydroxide was heated at reflux. Reaction aliquots (80 μL, 0.929% of the total) were withdrawn at the times indicated below, quenched with 25 ml of 0.05M pH 3 phosphate buffer and diluted to 100.0 ml with water and assayed by HPLC (Method C). The yields of 5 and 6 and their anomeric ratios (5:6) are tabulated below:

| Aliquot | Elapsed Time (Hrs.) | % Yield | % Yield | Ratio |
|---|---|---|---|---|
| 1 | 0.5 | 99.5 | 0.5 | 99.5:0.5 |
| 2 | 5.0 | 92.8 | 4.6 | 95:5 |
| 3 | 22.0 | 76.1 | 15.2 | 83:17 |
| 4 | 28.0 | 72.0 | 17.8 | 80:20 |
| 5 | 46.0 | 61.2 | 22.5 | 73:27 |
| 6 | 52.5 | 59.1 | 23.8 | 71:29 |
| 7 | 71.5 | 50.7 | 24.7 | 67:33 |
| 8 | 101.5 | 43.2 | 24.7 | 64:36 |
| 9 | 124.0 | 40.9 | 24.9 | 62:38 |

Method C: 25 cm×4.6 mm Apex ODS 5μ column. Flow rate: 0.8 ml/minute. Solvent A: methanol. Solvent B: 0.05M pH 3 phosphate buffer. Gradient: 0–10 minutes isocratic 100% of B; 10–15 minutes linear gradient from 100% of B to 50/50 of A/B; 15–19 minutes. isocratic 50/50 of A/B; 19–23 minutes linear gradient from 50/50 of A/B to 100% of B. The peak areas of 5 ($t_r$=6.6 minutes) and 6 ($t_r$=8.1 minutes) were compared to an external standard containing known quantities of authentic samples to provide the yields of each.

The present invention has been described in detail, including the perfected embodiments thereof. However, it will be appreciated that those skilled in the art, upon consideration of the present disclosure, may make modifications and/or improvements on this invention that fall within the scope and spirit of the inventions as set forth in the following claims.

What is claimed is:

1. A process for preparing a beta nucleoside anomer of the formula

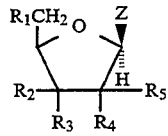

wherein $R_1$ is hydroxy; $R_2$ and $R_3$ are each selected from the group consisting of hydrogen, azide, lower alkyl, fluoro, hydroxy, and OB provided when one of $R_2$ and $R_3$ is hydroxy, the other of $R_2$ and $R_3$ cannot be fluoro, azide or hydroxy; $R_4$ and $R_5$ are each selected from the group consisting of hydrogen, azide, lower alkyl, fluoro, hydroxy, and OB, where each B is independently a lower alkyl or base-stable hydroxyl protecting group; provided when one of $R_4$ and $R_5$ is hydroxy, the other of $R_4$ and $R_5$ cannot be fluoro, azide or hydroxy; and Z is a nucleobase of the formula

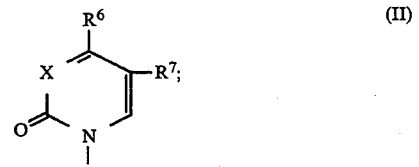

wherein X is selected from N and $CR_8$ where $R_8$ is hydrogen or lower alkyl; $R_6$ is selected from the group consisting of amino, lower alkyl amino, di(lower alkyl) amino, acyl amino, and N-acyl lower alkyl amino; and $R_7$ is selected from the group consisting of hydrogen, lower alkyl, fluoro and lower alkenyl; comprising contacting an alpha nucleoside of formula

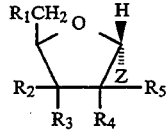

with a hydroxide base in an organic solvent.

2. The process of claim 1 wherein the hydroxide base is selected from the group consisting of alkali metal hydroxides, alkaline earth metal hydroxides or quaternary ammonium hydroxides.

3. The process of claim 2 wherein the hydroxide base is an alkali metal hydroxide selected from the group consisting of lithium hydroxide, potassium hydroxide, cesium hydroxide monohydrate or sodium hydroxide or an alkaline earth metal hydroxide such as barium hydroxide.

4. The process of claim 3 wherein the alkali metal hydroxide is selected from potassium hydroxide, sodium hydroxide or cesium hydroxide monohydrate.

5. The process of claim 4 wherein the alkali metal hydroxide is selected from potassium hydroxide or cesium hydroxide monohydrate.

6. The process of claim 1 wherein the amount of hydroxide base is from about 2 molar equivalents to about 40 molar equivalents.

7. The process of claim 6 wherein the amount of hydroxide base is from about 2.5 molar equivalents to about 5 molar equivalents.

8. The process of claim 1 wherein the hydroxide base concentration is from about 0.5 molar to about 5 molar.

9. The process of claim 8 wherein the hydroxide base concentration is from about 2 molar to about 4 molar.

10. The process of claim 1 wherein the solvent is selected from methanol, ethanol, 2-methoxyethanol, and mixtures thereof.

11. The process of claim 10 wherein the solvent is methanol.

12. The process of claim 10 wherein the solvent is a substantially anhydrous organic solvent.

13. The process of claim 1 wherein the process temperature is from room temperature to about 120° C.

14. The process of claim 13 wherein the process temperature is from about 40° C. to about 120° C.

15. The process of claim 14 wherein the process temperature is from about 40° C. to about 80° C.

16. The process of claim 1 wherein 1-(2'-deoxy-2',2'-difluoro-α-D-ribofuranosyl)-4-aminopyrimidin-2-one is contacted with anhydrous lithium hydroxide in methanol to form 1-(2'-deoxy-2',2'-difluoro-β-D-ribofuranosyl)-4-aminopyrimidin-2-one.

17. The process of claim 1 wherein of 1-(2'-deoxy-2',2'-difluoro-α-D-ribofuranosyl)-4-aminopyrimidin-2-one is contacted with anhydrous sodium hydroxide in methanol to form 1-(2'-deoxy-2',2'-difluoro-β-D-ribofuranosyl)-4-aminopyrimidin-2-one.

18. The process of claim 1 wherein 1-(2'-deoxy-2',2'-difluoro-α-D-ribofuranosyl)-4-aminopyrimidin-2-one is contacted with potassium hydroxide in ethanol to form 1-(2'-deoxy-2',2'-difluoro-β-D-ribofuranosyl)-4-aminopyrimidin-2-one.

19. The process of claim 1 wherein 1-(2'-deoxy-2',2'-difluoro-α-D-ribofuranosyl)-4-aminopyrimidin-2-one is contacted with barium hydroxide in methanol to form 1-(2'-deoxy-2',2'-difluoro-β-D-ribofuranosyl)-4-aminopyrimidin-2-one.

20. The process of claim 1 wherein 1-(2'-deoxy-2',2'-difluoro-α-D-ribofuranosyl)-4-aminopyrimidin-2-one is contacted with cesium hydroxide monohydrate in methanol to form 1-(2'-deoxy-2',2'-difluoro-β-D-ribofuranosyl)-4-aminopyrimidin-2-one.

21. The process of claim 1 wherein 1-(2'-deoxy-2',2'-difluoro-α-D-ribofuranosyl)-4-aminopyrimidin-2-one is contacted with potassium hydroxide in 2-methoxyethanol to form 1-(2'-deoxy-2',2'-difluoro-β-D-ribofuranosyl)-4-aminopyrimidin-2-one.

22. The process of claim 1 wherein 1-(2'-deoxy-2',2'-difluoro-α-D-ribofuranosyl)-4-aminopyrimidin-2-one is contacted with potassium hydroxide in methanol to form 1-(2'-deoxy-2',2'-difluoro-β-D-ribofuranosyl)-4-aminopyrimidin-2-one.

23. The process of claim 1 wherein 1-(2'-deoxy-2',2'-difluoro-α-D-ribofuranosyl)-4-aminopyrimidin-2-one is contacted with potassium hydroxide in methanol to form 1-(2'-deoxy-2',2'-difluoro-β-D-ribofuranosyl)-4-aminopyrimidin-2-one.

24. The process of claim 1 wherein 1-(2'-deoxy-2',2'-difluoro-α-D-ribofuranosyl)-4-aminopyrimidin-2-one is contacted with benzyltrimethylammonium hydroxide in methanol to form 1-(2'-deoxy-2',2'-difluoro-β-D-ribofuranosyl)-4-aminopyrimidin-2-one.

25. The process of claim 1 wherein an 81:19 alpha to beta mixture of 1-(2'-deoxy-2',2'-difluoro-D-ribofuranosyl)-4-aminopyrimidin-2-one is contacted with potassium hydroxide in methanol to form 1-(2'-deoxy-2',2'-difluoro-β-D-ribofuranosyl)-4-aminopyrimidin-2-one.

26. The process of claim 1 wherein 1-(2'-deoxy-α-D-ribofuranosyl)-4-aminopyrimidin-2-one is contacted with potassium hydroxide in methanol to form 1-(2'-deoxy-β-D-ribofuranosyl)-4-aminopyrimidin-2-one.

27. A process for preparing an alpha nucleoside anomer of the formula

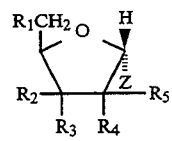

wherein $R_1$ is hydroxy; $R_2$ and $R_3$ are each selected from the group consisting of hydrogen, azide, lower alkyl, fluoro, hydroxy, and OB provided when one of $R_2$ and $R_3$ is hydroxy, the other of $R_2$ and $R_3$ cannot be fluoro, azide or hydroxy; $R_4$ and $R_5$ are each selected from the group consisting of hydrogen, azide, lower alkyl, fluoro, hydroxy, and OB, where each B is independently a lower alkyl or base-stable hydroxyl protecting group; provided when one of $R_4$ and $R_5$ is hydroxy, the other of $R_4$ and $R_5$ cannot be fluoro, azide or hydroxy; and Z is a nucleobase of the formula

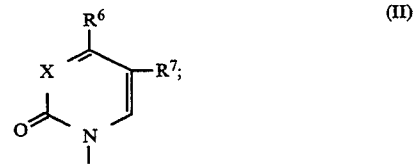

wherein X is selected from N and $CR_8$ where $R_8$ is hydrogen or lower alkyl; $R_6$ is selected from the group consisting of amino, lower alkyl amino, di(lower alkyl) amino, acyl amino, and N-acyl lower alkyl amino; and $R_7$ is selected from the group consisting of hydrogen, lower alkyl, fluoro and lower alkenyl; comprising contacting a beta nucleoside of formula

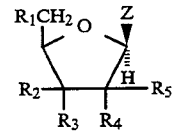

with a hydroxide base in an organic solvent.

28. The process of claim 27 wherein the hydroxide base is selected from the group consisting of alkali metal hydroxides, alkaline earth metal hydroxides or quaternary ammonium hydroxides.

29. The process of claim 28 wherein the hydroxide base is an alkali metal hydroxide selected from the group consisting of lithium hydroxide, potassium hydroxide, cesium hydroxide monohydrate or sodium hydroxide or an alkaline earth metal hydroxide such as barium hydroxide.

30. The process of claim 29 wherein the alkali metal hydroxide is selected from potassium hydroxide, sodium hydroxide or cesium hydroxide monohydrate.

31. The process of claim 30 wherein the alkali metal hydroxide is selected from potassium hydroxide or cesium hydroxide monohydrate.

32. The process of claim 27 wherein the amount of hydroxide base is from about 2 molar equivalents to about 40 molar equivalents.

33. The process of claim 32 wherein the amount of hydroxide base is from about 2.5 molar equivalents to about 5 molar equivalents.

34. The process of claim 27 wherein the hydroxide base concentration is from about 0.5 molar to about 5 molar.

35. The process of claim 34 wherein the hydroxide base concentration is from about 2 molar to about 4 molar.

36. The process of claim 27 wherein the solvent is selected from methanol, ethanol, 2-methoxyethanol, and mixtures thereof.

37. The process of claim 36 wherein the solvent is methanol.

38. The process of claim 27 wherein the solvent is a substantially anhydrous organic solvent.

39. The process of claim 27 wherein the process temperature is from room temperature to about 120° C.

40. The process of claim 39 wherein the process temperature is from about 40° C. to about 120° C.

41. The process of claim 40 wherein the process temperature is from about 40° C. to about 80° C.

42. The process of claim 27 wherein 1-(2'-deoxy-2',2'-difluoro-$\beta$-D-ribofuranosyl)-4-aminopyrimidin-2-one is contacted with potassium hydroxide in methanol to form 1-(2'-deoxy-2',2'-difluoro-$\alpha$-D-ribofuranosyl)-4-aminopyrimidin-2-one.

43. The process of claim 27 wherein 1-($\beta$-D-ribofuranosyl)-4-aminopyrimidin-2-one is contacted with potassium hydroxide in methanol to form 1-($\alpha$-D-ribofuranosyl)-4-aminopyrimidin-2-one

* * * * *